United States Patent
Springer et al.

(10) Patent No.: US 6,453,003 B1
(45) Date of Patent: Sep. 17, 2002

(54) APPARATUS FOR TRANSILLUMINATING OBJECTS

(75) Inventors: Klaus Springer, Selters-Eisenbach; Norbert Haunschild, Aarbergen, both of (DE)

(73) Assignee: Heimann Systems GmbH, Wiesbaden (DE)

( * ) Notice: Subject to any disclaimer, the term of this patent is extended or adjusted under 35 U.S.C. 154(b) by 0 days.

(21) Appl. No.: 09/746,559

(22) Filed: Mar. 28, 2001

(30) Foreign Application Priority Data

Dec. 13, 2000 (DE) .......................... 100 62 214

(51) Int. Cl.⁷ .............................................. G01N 23/02
(52) U.S. Cl. ................................ 378/57; 378/51; 378/9
(58) Field of Search ........................ 378/51, 57, 9

(56) References Cited

U.S. PATENT DOCUMENTS

| | | | | |
|---|---|---|---|---|
| 5,175,756 A | | 12/1992 | Pongratz et al. | 378/88 |
| 5,600,700 A | * | 2/1997 | Krug et al. | 378/57 |
| 5,642,393 A | | 6/1997 | Krug et al. | 378/57 |
| 5,940,468 A | * | 8/1999 | Huang et al. | 378/57 |
| 6,088,423 A | * | 7/2000 | Krug et al. | 378/57 |
| 6,122,344 A | * | 9/2000 | Beevor | 378/88 |

FOREIGN PATENT DOCUMENTS

| | | |
|---|---|---|
| DE | 198 23 448 A1 | 11/1999 |
| EP | 0 485 872 A2 | 5/1992 |
| EP | 0795746 A1 | 9/1997 |
| JP | 06265485 | 9/1994 |
| JP | 10267867 | 10/1998 |
| JP | 2000241368 | 9/2000 |
| WO | WO 97/12229 | 4/1997 |

\* cited by examiner

Primary Examiner—David P. Porta
Assistant Examiner—Therese Barber
(74) Attorney, Agent, or Firm—Birch, Stewart, Kolasch & Birch

(57) ABSTRACT

This invention concerns an apparatus to transilluminate objects.

In known apparatus (1) there are two radiation sources (10, 20) in a transport path of a transport device (3), below to the right and left, as well as a third radiation source (30) arranged horizontal to the transport path (3), with the two radiation sources (10, 20) lying close together, one behind the other. Three detector apparatus (11, 14, 31) are arranged opposite these radiation sources (10, 20, 30). Thus, a so called multi-view from three beam directions is created, with beam paths (FX1.1, FX2.2, FX3) extending perpendicular to a transport direction.

Contrary thereto, in the solution described herein, various radiation beam paths (FX1.1, FX1.2, FX2.1, FX2.2, FX3) cross so that not every beam radiation path extends perpendicular to the transport direction. This has the advantage that the apparatus can be structured in a space saving manner. In a particular embodiment, using three radiation sources (10, 20, 30) and five detector apparatus (11, 12, 21, 22, 31) in a single apparatus, an object (4) to be transilluminated is transilluminated from five different beam directions during its transport through a transillumination space (5) and a quasi 3-D (three-dimensional) model (6) of the object (4) is thereby, simultaneously created. In this regard, two of the detector apparatus (12, 21) are arrange angularly displaced from one another, within one another, to be directed toward corresponding rays (FX1.2, FX2.1) of the beam radiation sources (10, 20). With the help of signals obtained therefrom, in addition to the absorption rate, also the thickness or volume, and therefrom the density, of the items (4.1) in the object (4) can be determined. From the absorption rate and the density, the type of material found in the object (4) and the transilluminated items (4.1) can be exactly determined.

16 Claims, 3 Drawing Sheets

APPARATUS FOR TRANSILLUMINATING OBJECTS

BACKGROUND OF THE INVENTION

This invention concerns an apparatus for transilluminating objects as set forth in the preamble of patent claim 1.

An apparatus for recognizing particular explosives or other sought materials in luggage is described in European Patent document EP 0 485 872 A2. In this regard, the luggage is transilluminated from a plurality of directions with two or three X-ray sources in order to create therefrom substantially a three-dimensional density reconstruction of the luggage. The X-ray sources are thereby positionally offset from one another at the two upper corners of a cross-sectionally rectangular transport tunnel, through which luggage pieces are moved. In this regard, two X-ray sources are arranged closely near to and in front of one another. An L-shaped detector line is arranged opposite each of the X-ray sources. Through this apparatus a so-called multi-view is created from three beam directions, with all beam planes extending perpendicular to the transport direction.

International Patent Publication WO 9712229 describes a process and an apparatus for detecting smuggled goods, for example, explosive materials, drugs or money. In this case, a tomograph is used, with whose help a luggage piece indicated to be a smuggled good is viewed from various directions. In one embodiment, an X-ray generator is included in the tomograph. This X-ray generator is thereby attached to a C-arm. A detector device is also mounted on a C-arm, opposite the X-ray generator. The C-arm, and thereby the X-ray generator with the detector device, is moved in continuous planes for taking various pictures. From the determined absorption rate of the items in a luggage piece, an effective atom number $Z_{eff}$ is determined. Simultaneously, the mass and density of the detected item are determined by an algorithm.

An apparatus of the generic type of this invention is described in U.S. Pat. No. 6,088,423 A, which has at least three X-ray sources and three detector apparatus which, with the help of three different ray beam directions, creates a three dimensional image. In this regard, the radiation beam paths lie perpendicular to a transport direction. This uses a large amount of space and means that the apparatus will be large.

German Patent Publication DE198 23 448 A1 describes an apparatus to examine physical items using X-ray radiation in which a mask masks-through an appropriate portion of radiation so that a beam cone is created which is directed toward a linear shaped receiver arranged perpendicular to an object, and which creates time-displaced scan signals from different angular directions.

It is an object of this invention to provide an apparatus of the generic type described above which uses very little space.

This object is achieved by the limitations of patent claim 1.

SUMMARY OF THE INVENTION

According to principles of this invention, in order to decrease space requirements, at least two ionized radiation beams from different radiation sources are crossed over with at least one of these radiation beams not perpendicular to a transport direction or the object, and thereby at least two detector apparatus which at least partly cross over one another are directed toward these beams. In this manner, with the help of two beam sources and three detector apparatus, a spatial image of an object being transported can be created by the beams coming from different beam angles toward the object.

Beneficial enhancements are set forth in the dependent claims.

In a preferred variant, with the help of three radiation sources and five detector apparatus, an object to be transilluminated is transilluminated from at least five different directions during its transportation in the apparatus and a quasi 3-D (three dimensional) model of the object is simultaneously created. In this regard, preferably, two of the five detector apparatus are crossed within one another.

It is beneficial in one arrangement to have a front radiation source to the right and a following downstream radiation source to be left and below the transport apparatus. These are offset from one another and mounted along the transport path one behind the other. A third radiation source, contrary to this, is mounted above the transport apparatus. It is also, however, understood that the front radiation source can be arranged above the transport device and the two rear radiation sources can be mounted below the transport device.

Preferably, the detector apparatus are structured as L-shaped detector lines, which are formed of a plurality of detector pairs arranged one behind the other.

Preferably, the apparatus will be used in a multi-view system for automatically determining materials with X-ray beams, whereby, with help of obtain signals, in addition to absorption rate, the thickness or volume (and therefrom the density) of items in a object can be determined. From the absorption rate and the density then the type of material of items in an object which have just been transilluminated can be exactly determined.

BRIEF DESCRIPTION OF THE DRAWINGS

Further benefits can be seen from the following description of the drawings. Embodiments of the invention are shown in the drawings which include numerous features of the invention in combination. One of ordinary skill in the art can advantageously use the individual features for putting together practical further combinations.

IN THE DRAWINGS

Figure 1:
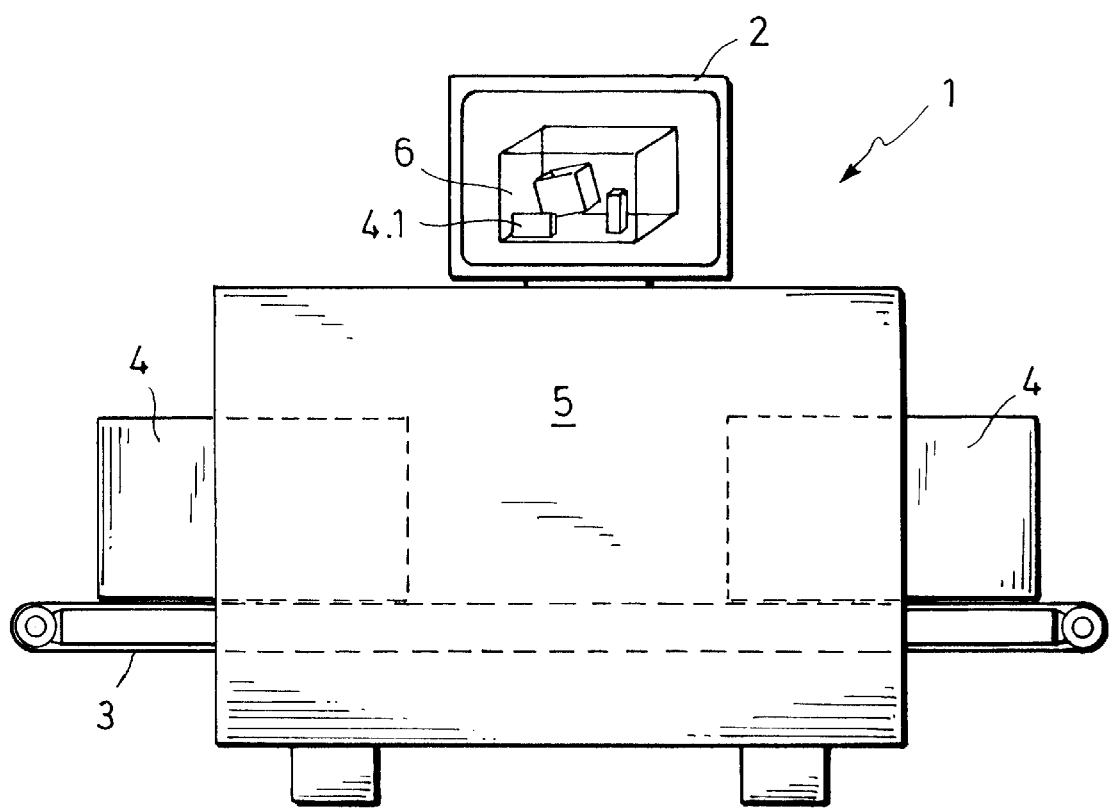
Figure 2:
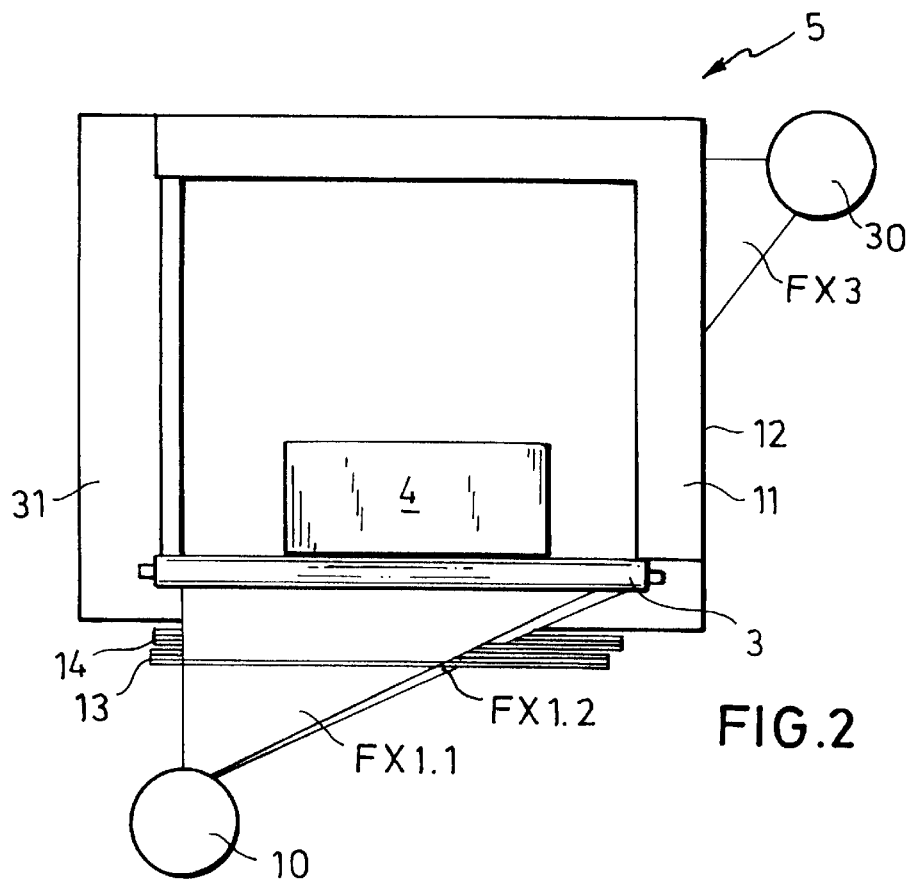
Figure 3:
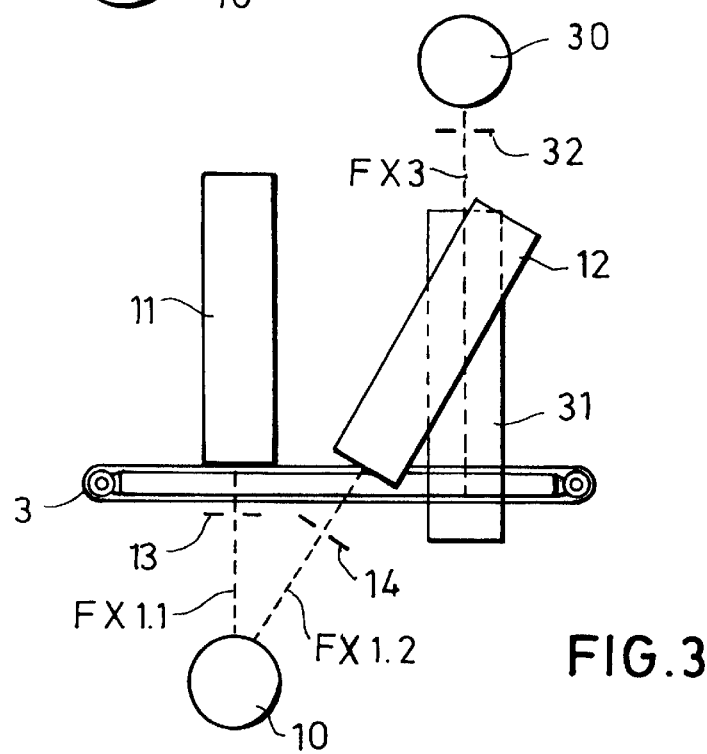
Figure 4:
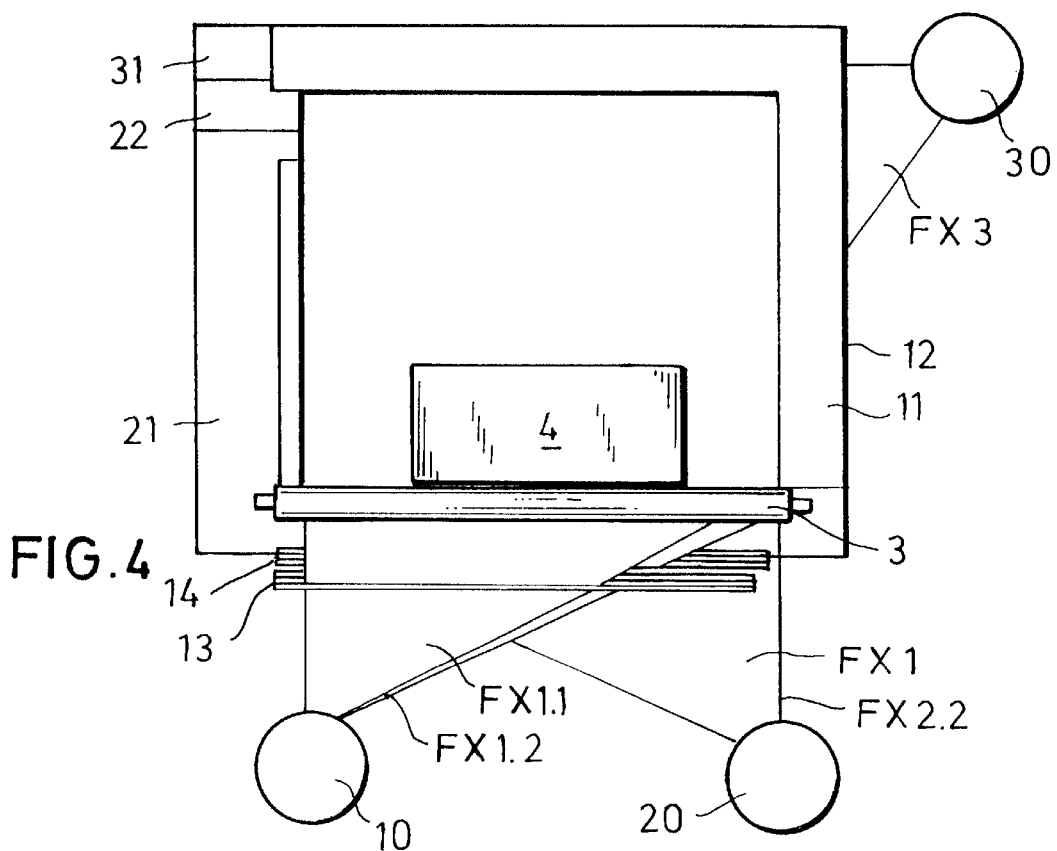

FIG. 1 is a conceptual schematic representation of an apparatus;

FIG. 2 is a front view of a transillumination space;

FIG. 3 is a side view of the transillumination space of FIG. 2 without an object;

FIG. 4 is a preferred variant of the apparatus; and

Figure 5:
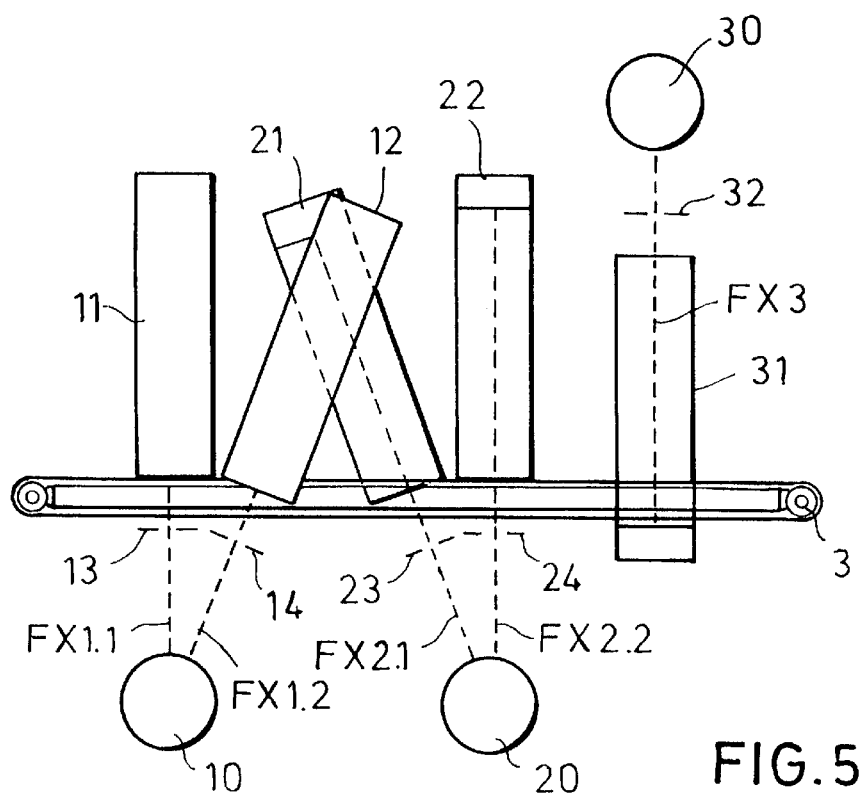

FIG. 5 is a side view of the transillumination space of FIG. 4, without an object.

DETAILED DESCRIPTION OF THE INVENTION

FIG. 1 shows a general view of an uncomplicated embodiment of an apparatus 1 of this invention for transillumination of an object 4, with a monitor 2, a transport track 3, an object 4 to be transilluminated, as well as a transillumination space 5. An image model of the object 4 is on a monitor 2 depicting items 4.1 contained therein.

Two different radiation sources 10, 30 are arranged in different planes about the transport track 3, as can be seen in a front view in FIG. 2 and in a side view in FIG. 3. Also, three detector apparatus 11, 12, 31 are positioned above or below the transport track 3. A double collimator, or two single collimators 13, 14 are arranged in front of the radiation source 10 to fade out two ionized rays or beams FX1.1, FX1.2, for example two X-ray beams of the same energy. A further collimator 32 is provided in front of the radiation source 30 which thereby fades out only one ionized beam FX3. Both of the detector structures 11, 12 are directed toward the beams FX1.1, FX1.2 of the common radiation source 10, such that they are arranged at an angle to one another. In a space-saving embodiment, the beam FX3 crosses one of the two beams FX1.1 or FX1.2 so that one of the two detector structures 11, 12 is angularly displaced to the detector structure 31, or tilted thereto, and is mounted to partly, or somewhat, be crossed therewith; with "crossed over" as used in this application also meaning that the detector structure 31 can be perpendicular to the tilted detector structure 11 or 12, in the above embodiment it being the detector structure 12. As used in this application, angularly displaced means that the beams FX1.1 and FX1.2 are radiated, or faded, to diverge from one another at a predetermined angle outwardly from a common focus point in the radiation source 10. By inter-crossing the detector structures 12, 31, a space between the two radiation sources 10, 30 can be reduced. A further space saving can be had if the radiation source 30 is mounted so that the beam FX3 also no longer extends perpendicular to the transport plane, rather comes from above directly opposite the beam FX1.2. In this case, the detector structure 31 and the detector structure 12 can be mounted to be still further interspersed into one another. Also an arrangement of the radiation source 30 beneath the transport track 30 is possible in the same manner.

In a preferred embodiment according to FIGS. 4 and 5, three radiation sources 10, 20, 30 are arranged in various planes, which is particularly clearly illustrated in FIG. 5. In this regard, there are five detector structures 11, 12, 21, 22, 31 above or below the transport track 3. These detector structures 11, 12, 21, 22, 31 are preferable structured as L-shaped detector lines. However, U-shaped detector line structures, as well as variations of both types, are possible.

The two front, relative to a transport direction, radiation sources 10, 20 are mounted to the right and the left, one after the other, preferably below the transport apparatus 3. These are assigned to the detector lines 11 and 12 as well as the detector lines 21 and 22 that are aligned with the radiation sources 10, 20 above the transport apparatus 3. These radiation sources 10, 20 are respectively allocated to the collimators 13, 14 and 23, 24 through which relevant portions of the beams are allowed to pass masks whereby two, angularly-displaced beams FX1.1 and FX1.2 as well as FX2.1 and FX2.2 are respectively created. These beams FX1.1 and FX1.2 as well as FX2.1 and FX2.2 are preferably formed as fanned rays. The collimators 13, 14 and 23, 24 are in this regard preferably structured as slit collimators. The angled arrangement of the slits of each of the slit collimators 13, 14 or 23, 24 to one another is, for example, at an angle of 30° to 90°. The collimators 13 and 24 are thereby preferably arranged almost parallel to the transport plane. With this arrangement, four beam directions are simultaneously created with only two radiation sources 10, 20.

The detector lines 12 and 21 are, as can be clearly seen in FIG. 5, angularly displaced to be aligned with the beams FX1.2 or FX2.1, whereby both detector lines 12, 21 are arranged to be crossed within one another. In this manner, a space saving and compact device 1 is provided. The more these detector lines 12, 21 are crossed within one another, the less space is necessary within the device 1. It is beneficial for the detector cells 12 and 21 to be crossed into one another at an angle of from 30° to around 60°.

A fifth beam FX3 for a fifth beam direction is created at a radiation source 30 with the help of a further collimator 32 in front of the radiation source 30. This third radiation source 30 is accordingly preferably arranged above, for example above right, the transport apparatus, for example in a rear space of the transillumination space 5. The collimator 32, which is formed as a slit collimator, for creating a preferably fan shaped beam FX3 extending perpendicular to a transport plane. The detector line 31, which cooperates with the X-ray generator 30, is mounted below the transport device 3.

The detector lines 11, 12, 21, 22, 31 of FIGS. 2 and 3 and FIGS. 4 and 5 are coupled, in a known manner, with an electronic processor (not shown in additional detail) for evaluating in a known manner signals created in the detector lines 11, 12, 21, 22, 31. Depending upon a decrease in intensity of the individual beams FX1.1–FX3, different magnitude signals are thereby generated. In this manner the object 4 to be transilluminated is transported along the transport track, or transport device 3, through the transillumination space 5 while the object 4 is transilluminated by 3 or 5 beams FX1.1–FX3 from three or five different directions. This transillumination can be made visible as a model 6 on the monitor 2 whereby the object 4 with the items 4.1 therein can be depicted according to an appropriate process, also three dimensionally.

Absorption, as well as the thickness or volumes of the items 4.1 in object 4 is determined from the signals created at the detector lines 11, 12, 21, 22, 31. From the thickness or the volume, the density can be determined. With these two measured quantities, the processor, with the help of reference quantities stored in the processor, can exactly determine the material type or types.

It should be understood that the series arrangement of the radiation sources 10, 20, 30 and the detector lines 11, 12, 21, 22, 31, as well as their mounting positions can be interchanged.

Further, the radiation sources 10, 20, 30 can be X-ray generators, gamma-radiation generators and the like. If the created beams FX1.1, FX1.2, FX2.1, FX2.2 as well as FX3 are X-ray beams, the detector structures 11, 12, 21, 22, 31 are made as scintillation detectors which are packaged as detector lines in a normal manner.

In addition to the already described ray fans, so called pencil beams can also, for example, be created in the normal manner by masks and used for transillumination of the objects 4.

The described arrangement of apparatus 1 is not limited to use in a hand luggage X-ray examination device. Such an arrangement can also be used for larger container X-ray examination installations and the like. Also, its use is not limited purely to flight safety.

What is claimed is:

1. Apparatus (1) for transilluminating objects (4) which, with the help of a transport device (3), are moved through a transillumination space (5) whereby there are at least first and second radiation sources (10, 20, 30) spaced from one another in a transport direction and at least first, second and third detector apparatus (11, 12, 21, 22, 31) mounted about the transport device (3), each of said detector apparatus being elongated with portions thereof extending about at least two sides of said transillumination space for receiving one of first, second and third ionized beams, wherein:

at least each of the first and second ionized beams (FX1.1, FX 1.2, FX2.1, FX2.2, FX3) comes from a different one of said first and second radiation sources (10, 20, 30); said first and second ionized beams intersect one another; one of said first and second ionized beams is at an angle not perpendicular to the transport direction of said transport device; at least said first and second detector apparatus (11, 12, 21, 22, 31) are aligned to receive said first and second ionized beams; and said first and second detector apparatus have portions thereof positioned on opposite sides of said transillumination space crossing one another along said first and second ionized beams (FX1.1, FX1.2, FX2.1, FX2.2, FX3) so that said first and second detector apparatus are interlaced with one another.

2. Apparatus as in claim 1, wherein:

said second and third ionized beams are created by masking radiation with a collimator means from said second radiation source (10, 20) for creating at least said second and third ionized beams (FX1.1, FX1.2, FX2.1, FX2.2, FX3).

3. Apparatus as in claim 1, further comprising:

a third radiation source (10, 20, 30) and fourth and fifth detector apparatus; said first, second and third radiation sources cooperating with said first, second, third, fourth and fifth detector apparatus (11, 12, 21, 22, 31), such that said third, fourth and fifth detector apparatus (11, 12, 21, 22) are directed toward said third and fourth and fifth ionized beams, each of said third, fourth and fifth ionized beams being generated from a different one of said first, second and third radiation sources.

4. Apparatus as in claim 1, wherein:

said second and third ionized beams are generated by said second radiation source using a collimator means including two masks each mask respectively arranged in front of said second radiation source (10, 20), which is a common point of said second and third ionized beams.

5. Apparatus according to claim 4, wherein:

the masks of said collimator means are structured as slit collimators which are angularly arranged to one another, respectively in an angular range of 30° to 90°.

6. Apparatus according to claim 1, wherein:

one of said slit collimators (13, 14, 23, 24) is arranged substantially parallel to a transport path of the transport device.

7. Apparatus according to claim 3, wherein said apparatus further comprises:

a collimator (32) having at least one mask positioned for forming a third radiation source (30) extending substantially perpendicular to the transport path (3).

8. Apparatus according to claim 7, wherein said collimator (32) is a slit collimator.

9. Apparatus as in claim 1, wherein:

is further included a third radiation source, and wherein front two, relative to the transport direction, of said radiation sources (10, 20) are arranged below the transport device (3), to the right and the left thereof respectively, whereby they are mounted to be offset from one another, one behind the other, in the transport direction, and a rear-most of said radiation sources is arranged above the transport device (3) in a rear portion of the transillumination space.

10. Apparatus as in claim 1, wherein said first, second, and third detector apparatus (11, 12, 21, 22, 31) are structured as scintillation detectors which are packaged as elongated detector lines.

11. Apparatus as in claim 10, wherein said first, second, and third detector lines (11,12, 21, 22, 31) are structured to be L-shaped.

12. Apparatus (1) for transilluminating objects (4) which, with the help of a transport device (3), are moved through a transillumination space (5) whereby there are at least three radiation sources (10, 20, 30) and at least five detector apparatus (11, 12, 21, 22, 31) mounted about the transport device (3), said apparatus comprising:

at least two ionized beams (FX1.1, FX1.2, FX2.1, FX2.2, FX3) from different radiation sources (10, 20, 30) crossing one another, with at least two detector apparatus (11, 12, 21, 22, 31) also crossing one another along these ionized beams (FX1.1, FX 1.2, FX2.1, FX2.2, FX3) wherein three radiation sources (10, 20, 30) cooperate with five detector apparatus (11, 12, 21, 22, 31), with four of the detector apparatus (11, 12, 21, 22) being directed toward four beams (FX1.1, FX 1.2, FX2.1, FX2.2) generated from two of the radiation sources whereby: two of these detectors apparatus (12, 21) cross within one another so that each of these two detector apparatus is directed toward one of the two beams (FX1.2, FX2.1) of the two radiation sources (10, 20) with these two beams (FX1.2, FX2.1) crossing one another.

13. The claim according to claim 12, said apparatus further comprising: a collimator (32) corresponding to a third radiation source (30) extending perpendicular to the transport path (3).

14. The claim according to claim 13, wherein the collimator (32) is a slit collimator.

15. Apparatus (1) for transilluminating objects (4) which, with the help of a transport device (3), are moved through an transillumination space (5) whereby there are at least three radiation sources (10, 20, 30) and at least three detector apparatus (11, 12, 21, 22, 31) mounted about the transport device (3), said apparatus comprising:

at least two ionized beams (FX1.1, FX 1.2, FX2.1, FX2.2, FX3) from different radiation sources (10, 20, 30) crossing one another, with at least two detector apparatus (11, 12, 21, 22, 31) also crossing one another along these ionized beams (FX1.1, FX1.2, FX2.1, FX2.2, FX3) wherein front two of the at least three radiation sources (10, 20) are arranged below the transport device (3), to the right and the left thereof respectively, whereby they are mounted to be offset from one another, one behind the other in the transport direction, and a rear-most of said radiation sources is arranged above the transport device (3) in a rear portion of the transillumination space.

16. The claim according to claim 15 wherein the detector apparatus are detector lines (11,12, 21, 22, 31) structured to be L-shaped.

\* \* \* \* \*